(12) United States Patent
Cipriani

(10) Patent No.: US 6,417,003 B1
(45) Date of Patent: Jul. 9, 2002

(54) METHOD AND KIT FOR EPITHELIAL CANCER SCREENING

(75) Inventor: Pier J. Cipriani, Newtown, PA (US)

(73) Assignee: Zila, Inc., Phoenix, AZ (US)

( * ) Notice: Subject to any disclaimer, the term of this patent is extended or adjusted under 35 U.S.C. 154(b) by 0 days.

(21) Appl. No.: 07/978,670

(22) PCT Filed: Jan. 14, 1993

(86) PCT No.: PCT/US93/00352

§ 371 (c)(1),
(2), (4) Date: Sep. 13, 1994

(87) PCT Pub. No.: WO94/16325

PCT Pub. Date: Feb. 21, 1994

(51) Int. Cl.[7] ............................................... G01N 33/48
(52) U.S. Cl. ........................... 436/64; 422/61; 424/9.7
(58) Field of Search ............................ 422/61; 436/64; 206/569; 424/9.1, 9.7, 9.8

(56) References Cited

U.S. PATENT DOCUMENTS

| 3,743,088 | A | * | 7/1973 | Henkin | 206/569 |
| 4,321,251 | A | * | 3/1982 | Mashberg | 424/9.7 |
| 4,977,177 | A | * | 12/1990 | Bommer et al. | 424/9.61 |
| 5,018,531 | A | * | 5/1991 | Hartman | 128/774 |
| 5,112,758 | A | * | 5/1992 | Fellman et al. | 436/8 |
| 5,240,415 | A | * | 8/1993 | Haynie | 433/216 |
| 5,372,801 | A | * | 12/1994 | Malmros et al. | 427/7.1 |

* cited by examiner

*Primary Examiner*—Maureen M. Wallenhorst
(74) *Attorney, Agent, or Firm*—Drummond & Duckworth

(57) ABSTRACT

A method and kit for screening patients for oral epitheleal cancer. The clinician is provided with a kit containing the staining dye test solution in preselected concentration and volume in prepackaged form, to permit the clinician to dispense the solution directly from the package without diluting or reconstituting before application to oral tissue.

2 Claims, 1 Drawing Sheet

METHOD AND KIT FOR EPITHELIAL CANCER SCREENING

This invention relates to improved methods of screening patients for epithelial cancer.

In another respect, the invention relates to a kit for use in screening patients to detect possible epithelial cancer.

More particularly, the invention pertains to a kit for use in screening patients for epithelial cancer, which can be used by medical personnel without highly specialized training.

In yet another respect, the invention pertains to a kit for use in screening patients for epithelial cancer, which places all of the necessary materials in "ready-to-use" form at the immediate disposal of clinical personnel, without requiring time-consuming or complicated mixing-storage-dispensing-measuring steps.

Various procedures are known for screening patients for epithelial cancer, especially for detecting suspected cancerous and precancerous sites on the mucosa such as the oral mucosa. Such procedures generally employ a dye which preferentially stains RNA-rich tissues, which have been recognized as characteristic of cancerous and precancerous conditions. For example, the U.S. Pat. No. 4,321,251 to Mashberg discloses such a procedure. The procedure of Mashberg involves sequential washes, rinses and applications of water, diluted acetic acid and a solution of toluidine blue-O dye in the mouth to detect cancerous and precancerous conditions of the oral mucosa. This wash-rinse-application-rinse-wash procedure is then repeated when a suspected site is detected, to reduce the number of false positives.

It would be highly advantageous to screen all patients for epithelial cancer during routine office visits, such as visits to dental offices for teeth cleaning, etc. However, methods of screening for epithelial cancer such as the Mashberg procedure have not achieved routine use, partly because the mixing, measuring and dispensing the solutions required is too time consuming to be done for each patient by the dentist and such procedures require some training and experience beyond that normally possessed by para-professional assistants.

It would therefore be desirable to provide an improved method for screening patients for epithelial cancer which is simplified and especially adapted to promote routine screening as the adjunct to normal visits by the patient to medical or dental offices for other reasons.

Accordingly, the principal object of the present invention is to provide such improved screening methods.

Yet another object of the invention is to provide apparatus which encourages such routine testing, by minimizing the time and complications which formerly discouraged such routine testing by medical and dental professionals.

These and other, further and more specific objects and advantages of the present invention will be apparent to those skilled in the art from the following detailed description thereof, taken in conjunction with the drawing, which depicts a kit of components assembled in accordance with the principles of one embodiment of the invention.

Briefly, in accordance with the invention, I provide methods and apparatus for screening patients for epithelial cancer.

My method is an improvement of prior art screening methods which include the steps of sequentially applying to suspected cancerous or precancerous sites preselected volumes of at least two liquid testing reagents of preselected concentrations. My improved method comprises providing such reagents to the administering clinician in prepackaged form, each of said reagents packaged to contain the preselected volume thereof at the preselected concentration thereof, to permit direct dispensation of each such reagent directly from its package for use in accordance with the screening procedure, without further mixing or measuring steps.

In accordance with another embodiment of the invention I provide a diagnostic kit for performing routine screening procedures to detect possible epithelial cancer. Such procedures include the steps of sequentially applying preselected volumes of at least two testing reagents of preselected concentrations to suspected cancerous or precancerous sites. The kit includes a separate package of each of the testing reagents. Each of the packages contains the preselected volume of the reagent in the preselected concentration thereof.

The drawing.

Figure 1:
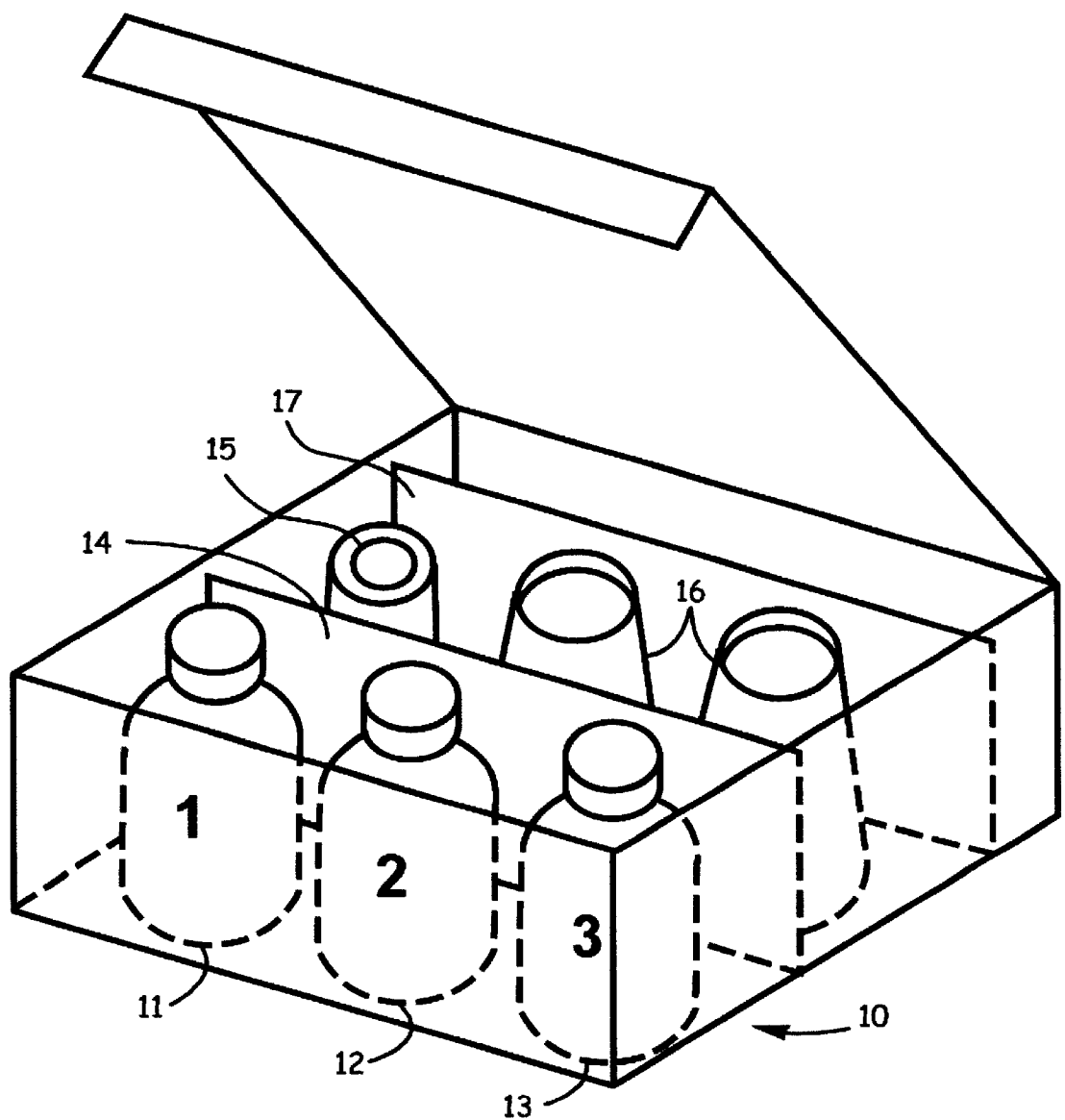
FIG. 1 depicts a kit of components assembled in accordance with the principles of one embodiment of the invention.

The kit is conveniently contained in a single box 10 which contains all of the components necessary for screening a single patient for oral epithelial cancer. The components include three bottles 11, 12 and 13, with single use cups. Bottle 11 contains 10 cc of a pre-rinse solution which is a 1% solution of acetic acid, used to adjust the Ph of the oral cavity and wash away food particles and the like. Bottle 12 contains 10 cc. of a 1% solution of toluidine blue-O. Bottle 13 contains 30 cc. of 1% acetic acid solution post-rinse, which is used to remove excess toluidine blue-O dye from the mouth. In accordance with the presently preferred embodiment, I also include other optional components in the kit such as an oral diagram sheet 14, on which the clinician can record the location of any suspected cancerous sites for later reference, a patient bib 15, cups 16 for administering water washes and a clinical information reply card 17 which is used to confirm the effectiveness of the procedure.

As will be apparent to those skilled in the art, my invention is not limited to a specific treatment method or specific solutions. Instead, it is generally applicable to any epithelial cancer detection procedures which employ a plurality of testing reagents, without limitation on the specific testing reagents employed.

DETAILED DESCRIPTION OF THE INVENTION

Having described my invention in such terms as to enable those skilled in the art to understand and practice it, and having identified the presently preferred embodiments thereof,

I claim:

1. In a method for screening patients for oral epitheleal cancer by an administering clinician, according to a procedure which includes the steps of said clinician sequentially applying to oral tissues preselected volumes of at least two liquid testing solutions, a first one of said solutions containing a preselected concentration of a staining dye reagent, and a second one of said solutions containing a preselected concentration of a rinsing reagent, the improvement comprising providing said liquid testing solutions to said administering clinician in prepackaged form, at least said first solution being contained in a separate package containing said preselected volume thereof at said preselected concentration thereof, to permit said clinician to dispense at least said first solution for oral application directly from its said package, in accordance with said procedure, without diluting or reconstituting at least said first solution before application thereof to oral tissue.

2. A diagnostic kit for performing routine screening procedures to detect possible oral epitheleal cancer, said procedures including the steps of sequentially applying to oral tissue preselected volumes of at least two liquid testing solutions, a first one of said solutions containing a preselected concentration of a staining dye reagent, and a second one of said solutions containing a preselected concentration of a rinsing reagent, said kit including a separate package for at least said first solution, said package for said first solution containing said preselected volume thereof, in said preselected concentration thereof.

* * * * *